(12) United States Patent
Guo et al.

(10) Patent No.: US 6,689,808 B2
(45) Date of Patent: Feb. 10, 2004

(54) SUBSTITUTED PHTHALIDES, A PROCESS FOR THEIR PREPARATIONS AND PHARMACEUTICAL COMPOSITIONS CONTAINING THEM

(75) Inventors: Zongru Guo, Beijing (CN); Fengming Chu, Beijing (CN); Juntian Zhang, Beijing (CN); Guangzhong Yang, Beijing (CN); Bailing Xu, Beijing (CN); Xinyi Niu, Beijing (CN); Zhihong Ren, Beijing (CN); Pierre Lestage, La Celle Saint Cloud (FR); Pierre Renard, Le Chesnay (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/312,650

(22) PCT Filed: Jun. 27, 2001

(86) PCT No.: PCT/IB01/01535

§ 371 (c)(1),
(2), (4) Date: Dec. 26, 2002

(87) PCT Pub. No.: WO02/00638

PCT Pub. Date: Jan. 3, 2002

(65) Prior Publication Data

US 2003/0220393 A1 Nov. 27, 2003

(30) Foreign Application Priority Data

Jun. 28, 2000 (CN) .......................... 00119329 A

(51) Int. Cl.$^7$ .............................. A61K 31/36
(52) U.S. Cl. .................. 514/465; 514/462; 514/466; 549/304; 549/307
(58) Field of Search ................. 549/304, 307; 514/462, 465, 466

(56) References Cited

U.S. PATENT DOCUMENTS 4,855,320 A * 8/1989 Chatterjee et al. .......... 549/313

FOREIGN PATENT DOCUMENTS

| EP | 151964 | * 8/1985 |
| EP | 341081 | * 11/1989 |

OTHER PUBLICATIONS

Copies of the reference were provided by applicant.*

* cited by examiner

*Primary Examiner*—Amelia Owens
(74) *Attorney, Agent, or Firm*—The Firm of Hueschen and Sage

(57) ABSTRACT

The invention relates to compounds of formula (I):

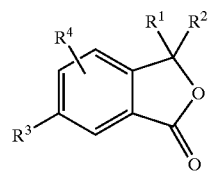

wherein
$R^1$ represents alkyl or ureido,
$R^2$ represents alkyl or hydrogen, or $R^1$ and $R^2$ together form a 5- or 6-membered ring,
$R^3$ represents CN, $NO_2$, $NR_aR'_a$, $NR_aSO_2R'_a$, $NR_aCZR^5$ or $CZNR_aR'_a$,
$R^4$ represents hydrogen or $R^3$,
and medicinal products containing the same which are useful in treating or preventing epilepsy and neurodegenerative diseases.

16 Claims, No Drawings

SUBSTITUTED PHTHALIDES, A PROCESS FOR THEIR PREPARATIONS AND PHARMACEUTICAL COMPOSITIONS CONTAINING THEM

The present invention relates to new substituted phthalides, to a process for their preparation and to pharmaceutical compositions containing them.

Epilepsy is a collective term used to describe a group of chronic convulsive disorders having in common the occurrence of brief episodes (seizures) associated with loss or disturbance of consciousness. There are many anti-epilepsy drugs available in clinical applications, such as Phenobarbital, Phenytoin, Zolenzepine, Ethosuximide, Paramethadione, Valproic acid. Although these medicines are able to protect patients from convulsion of various epilepsies to different extents, adverse effects and tolerance usually prevent long-term therapy. New compounds with novel structural features and with new mechanisms of action are needed in order to improve the therapeutic effect and eliminate or reduce the adverse response.

The compounds of the present invention are new, devoid of any toxicity and exhibit interesting pharmacological properties as anti-convulsants. Furthermore, they are potent calcium and sodium channel blockers conferring on them neuroprotective and cognition-enhancing properties.

More specifically, the present invention relates to compounds of formula (I):

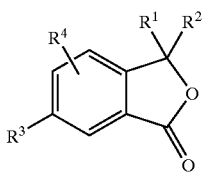

(I)

wherein:
$R^1$ represents a linear or branched $(C_1-C_{12})$alkyl group or a ureido group,
$R^2$ represents a hydrogen atom or a linear or branched $(C_1-C_{12})$alkyl group,
or $R^1$ and $R^2$, together with the carbon atom carrying them, form a cycloalkyl group containing 5 or 6 carbon atoms,
$R^3$ represents a group CN, $NO_2$, $NR_aR'_a$, $NR_aSO_2R'_a$, $NR_aCZR^5$ or $CZNR_aR'_a$ wherein Z represents an oxygen or sulphur atom and $R^5$ represents a group $OR_a$, $R_a$ or $NR_aR'_a$ (wherein $R_a$ and $R'_a$, which may be the same or different, represent a hydrogen atom or a linear or branched $(C_1-C_6)$alkyl group, a $(C_3-C_8)$cycloalkyl group, a $(C_3-C_8)$cycloalkyl-$(C_1-C_6)$alkyl group in which the alkyl moiety is linear or branched, a phenyl group or a phenyl-$(C_1-C_6)$alkyl group in which the alkyl moiety is linear or branched),
$R^4$ represents a hydrogen atom or a group $R^3$ as defined hereinbefore,
it being understood that:
the phenyl or phenylalkyl groups may be substituted on the benzene ring by one or more substituents selected from linear or branched $(C_1-C_6)$alkyl, hydroxy, linear or branched $(C_1-C_6)$alkoxy, amino, linear or branched $(C_1-C_6)$alkylamino, di-$(C_1-C_6)$alkylamino in which each allyl moiety is linear or branched, $NO_2$ and halogen atoms,
the alkyl group may be substituted by one or more substituents selected from hydroxy, carboxy, linear or branched $(C_1-C_6)$alkyl, linear or branched $(C_1-C_6)$alkoxy and halogen atoms,
the cycloalkyl and cycloalkylalkyl groups may be substituted on the cyclic moiety by one or more substituents selected from hydroxy, carboxy, linear or branched $(C_1-C_6)$alkoxy and halogen atoms,
and provided that the compound of formula (I) cannot represent 3-methyl-, 3-ethyl-, 3,3-diethyl- or 3,3-diethyl-6-nitro-phthalide or 3-methyl- or 3,3-dimethyl-6-amino-phthalide or 3,3-dimethyl-6-(dimethylamino)-phthalide, their enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may be mentioned, without implying any limitation, sodium hydroxide, potassium hydroxide, triethylamine, tert-butylamine etc.

Preferred compounds of the invention are compounds of formula (I) wherein $R^4$ represents a hydrogen atom.

The group $R^1$ is preferably a linear or branched $(C_1-C_{12})$ alkyl group and, more especially, the groups methyl, ethyl and n-butyl, or $R^1$ and $R^2$, together with the carbon atom carrying them, form a ring having 5 or 6 carbon atoms.

Advantageously, the invention relates to compounds of formula (I) wherein $R^3$ represents a nitro group or a group $NR_aR'_a$ (wherein $R_a$ and $R'_a$ are as defined hereinbefore) such as, for example, the groups amino, formamido, isopropylanino or dimethylamino.

Even more preferably, the invention relates to compounds of formula (I) that are:
6-amino-3-butyl-phthalide,
(+)-(3R)-6-amino-3-butyl-phthalide,
3-butyl-6-isopropylamino-phthalide,
6-amino-3,3-spiro-tetramethylene-phthalide,
3-butyl-6-formamido-phthalide,
6-amino-3,3-diethyl-phthalide.

The enantiomers and diastereoisomers, as well as the addition salts with a pharmaceutically acceptable acid or base, of the preferred compounds of the invention form an integral part of the invention.

The invention relates also to a process for the preparation of compounds of formula (I), which process is characterised in that there is used as starting material a compound of formula (II):

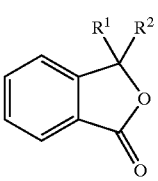

(II)

wherein R¹ and R² are as defined hereinbefore, which is nitrated under conditions of electrophilic substitution to yield the compound of formula (I/a), a particular case of the compounds of formula (I):

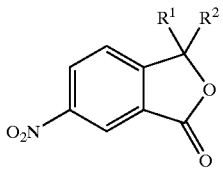

(I/a)

wherein R¹ and R² are as defined hereinbefore, which may be hydrogenated chemically or by means of catalytic hydrogenation to obtain the compound of formula (I/b), a particular case of the compounds of formula (I):

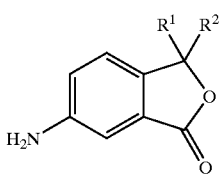

(I/b)

wherein R¹ and R² are as defined hereinbefore,
which may be:

either subjected to the action of one or two molecules of a compound of formula (III):

(III)

wherein $R^1_a$ may take any of the meanings of $R_a$ except for a hydrogen atom and X represents a leaving group such as a halogen atom or a tosyl group, to yield the compound of formula (I/c), a particular case of the compounds of formula (I):

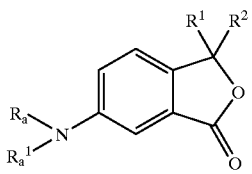

(I/c)

wherein R¹, R², $R_a$ and $R^1_a$ are as defined hereinbefore,
or subjected to the action of a compound of formula (IV):

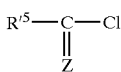

(IV)

wherein Z is as defined hereinbefore and $R'^5$ represents a group $R_a$ or $OR_a$ (wherein $R_a$ is as defined hereinbefore), to obtain the compound of formula (I/d), a particular case of the compounds of formula (I):

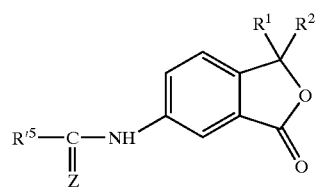

(I/d)

wherein R¹, R², Z and $R'^5$ are as defined hereinbefore, which may be subjected to the action of a compound of formula (III) to yield the compound of formula (I/e), a particular case of the compounds of formula (I):

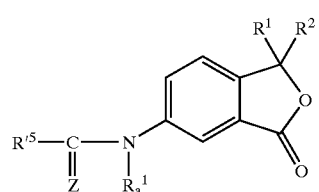

(I/e)

wherein R¹, R², R⁵, $R'^5$ and Z are as defined hereinbefore, or subjected to the action of a compound of formula (V):

(V)

wherein Z and $R_a$ are as defined hereinbefore, to obtain the compound of formula (I/f), a particular case of the compounds of formula (I):

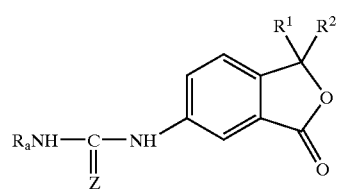

(I/f)

wherein R¹, R², Z and $R_a$ are as defined hereinbefore, which may be subjected to the action of a compound of formula (III) to yield the compound of formula (I/g), a particular case of the compounds of formula (I):

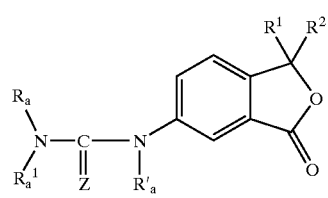

(I/g)

wherein R¹, R², $R_a$, $R'_a$, $R^1_a$ and Z are as defined hereinbefore, or subjected to the successive action of nitrous acid and then CuCN to yield the compound of formula (I/h), a particular case of the compounds of formula (I):

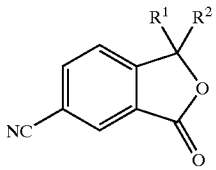
(I/h)

wherein $R^1$ and $R^2$ are as defined hereinbefore, which may be hydrolysed in an acid or basic medium to yield the compound of formula (I/i), a particular case of the compounds of formula (I):

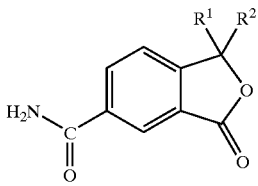
(I/i)

wherein $R^1$ and $R^2$ are as defined hereinbefore, which may be subjected to the action of a compound of formula (III) to obtain the compound of formula (I/j), a particular case of the compounds of formula (I):

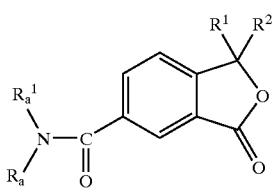
(I/j)

wherein $R^1$, $R^2$, $R_a$ and $R^1_a$ are as defined hereinbefore, which compounds of formulae (I/i) and (I/j) may be subjected to the action of a thionating agent such as Lawesson's reagent to yield the compound of formula (I/k), a particular case of the compounds of formula (I):

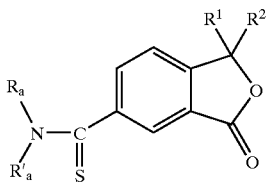
(I/k)

wherein $R^1$, $R^2$, $R_a$ and $R'_a$ are as defined hereinbefore, which compounds of formulae (I/a) to (I/k) may be subjected to a second nitration and optionally also to the entire sequence of reactions described hereinbefore to obtain the compound of formula (I/l), a particular case of the compounds of formula (I):

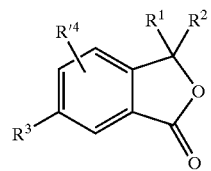
(I/l)

wherein $R^1$, $R^2$ and $R^3$ are as defined hereinbefore and
$R'^4$ may take any of the meanings of the group $R^3$,
the compounds of formulae (I/a) to (I/l) constituting the totality of the compounds of formula (I), which may be purified according to a conventional separation technique, are converted, if desired, into their addition salts with a pharmaceutically acceptable acid or base and are separated, where appropriate, into their isomers according to a conventional separation technique.

The compounds of formula (II) are either commercially available or readily accessible to the person skilled in the art by means of conventional chemical reactions.

In particular, compounds of formula (II) may be obtained:
starting from 2-formyl-benzoic acid, which is condensed with one or two molecules of Grignard reagents RMgX' wherein R represents a linear or branched ($C_1$–$C_{12}$) alkyl group and X' represents a halogen atom,
or starting from phthalic anhydride, which is condensed with:
a compound of formula RCOCl or the corresponding anhydride (wherein R is as defined hereinbefore), followed by catalytic or chemical hydrogenation,
or a compound of formula X'—Mg—$(CH_2)_n$—Mg—X' wherein X' is as defined hereinbefore and n is 4 or 5.

In addition to the fact that the compounds of the present invention are new, they exhibit very interesting pharmacological properties and are devoid of any toxicity.

They have anti-convulsant properties rendering them of use as anti-epileptic compounds. Results have shown that they are new calcium antagonists and can be used as a basis for elucidating the anti-epileptic mechanism.

Compounds of the invention furthermore exhibit potent neuroprotective effects and cognition-enhancing properties rendering them of use in:
the treatment of cognitive deficiencies associated with ageing and with neurodegenerative disease such as Alzheimer's disease, Parkinson's disease, Pick's disease, Korsakoff's disease and frontal lobe and subcortical dementias,
the prophylactic treatment of chronic neurodegenerative diseases,
and in the prevention of recurrence of cerebral ischemia The invention relates also to pharmaceutical compositions comprising as active ingredient at least one compound of formula (I) together with one or more appropriate, inert, non-toxic excipients. Among the pharmaceutical compositions according to the invention there may be mentioned more especially those that are suitable for oral parenteral (intravenous or subcutaneous) and nasal administration, tablets or sugar coated tablets, sublingual tablets, gelatin capsules, lozenges, suppositories, creams, ointments, dermal gels, injectable preparations, drinkable suspensions etc.

The dosage used can be adapted to the nature and the severity of the disorder, the administration route and the age and weight of the patient The dosage varies from 0.01 mg to 1 g per day in one or more administrations.

The following Examples illustrate the invention but do not limit it in any way.

The following Preparations yield compounds of the invention or synthesis intermediates that are useful in the preparation of compounds of the invention.

Preparation 1: 3-Butylphthalide

A dry three-necked flask is charged with 16.0 g (0.658 mol) of magnesium turnings, which are covered with anhydrous ether. A small portion of n-butyl bromide is added dropwise to the mixture to initiate the reaction. The addition of n-butyl bromide is continued until the magnesium turnings are digested completely; the total amount of n-butyl bromide added is 82 g (0.599 mol). The reaction mixture is then heated under reflux for 1 hour. To the cooled Grignard reagent there is added, dropwise, a solution of 36.0 g (0.24 mol) of o-phthalaldehydic acid in 200 ml of anhydrous tetrahydrofuran in 1 hour. The reaction mixture is refluxed for 1 hour and cooled. To this mixture there are carefully added 250 ml of saturated ammonium chloride solution. Concentrated hydrochloric acid is added to make the mixture pH=2. The ethereal phase is separated off and the aqueous phase is extracted three times with ether. The combined organic phase is dried over sodium sulphate and evaporated. The residue is distilled in vacuo to give the title compound.

Boiling point: 144–148° C./2 mmHg.

Preparation 2: 3-Ethylphthalide

Analogously to the method described in Preparation 1, reaction of 30 g (0.20 mol) of o-phthalaldehydic acid, 65.38 g (0.60 mol) of ethyl bromide and 16.0 g (0.66 mol) of magnesium turnings is carried out to give the title compound.

Boiling point: 110–125° C./2 mmHg; Elemental microanalysis:

|              | C     | H    |
|--------------|-------|------|
| % calculated: | 74.06 | 6.21 |
| % found:      | 73.93 | 5.89 |

Preparation 3: 3-Hexylphthalide

Analogously to the method described in Preparation 1, reaction of 8.6 g (0.0573 mol) of phthalaldehydic acid, 28.4 g (0.172 mol) of n-hexyl bromide and 4.6 g (0.189 mol) of magnesium turnings is carried out to give the title compound.

Boiling point: 182–185° C./4 mmHg; Elemental microanalysis:

|              | C     | H    |
|--------------|-------|------|
| % calculated: | 77.03 | 8.31 |
| % found:      | 77.30 | 7.99 |

Preparation 4: 3-Octylphthalide

Analogously to the method described in Preparation 1, reaction of 10 g (0.067 mol) of o-phthalaldehydic acid, 38.8 g (0.201 mol) of n-octyl chloride and 5.3 g (0.221 mol) of magnesium turnings is carried out to give the title compound.

Boiling point: 174–180° C./2 mmHg; Elemental microanalysis:

|              | C     | H    |
|--------------|-------|------|
| % calculated: | 79.98 | 9.00 |
| % fouud:      | 77.88 | 9.10 |

Preparation 5: 3,3-Diethylphthalide 3.6 g (0.15 mol) of magnesium turnings are reacted with 15.26 g (0.14 mol) of ethyl bromide in anhydrous ether to make the Grignard reagent, to which there is added, dropwise, a solution of 10.0 g (0.068 mol) of phthalic anhydride in anhydrous THF. After completing the addition, the reaction mixture is refluxed for 2 hours. To the cooling mixture there is added a saturated solution of ammonium chloride and the mixture is acidified with concentrated hydrochloric acid. The acidified liquid is extracted several times with ether. The combined organic phase is washed with water and dried over sodium sulphate. The solvent is removed and the residue is crystallised from petroleum ether to give 4.5 g of the title compound.

Boiling point: 110–125° C./2 mmHg; Elemental microanalysis:

|              | C     | H    |
|--------------|-------|------|
| % calculated: | 75.76 | 7.44 |
| % found:      | 76.03 | 7.32 |

Preparation 6: 3,3-Spiro-tetramethylenephthalide

Analogously to the method described in Preparation 5, reaction of 5.4 g (0.22 mol) of magnesium turnings, 21.6 g (0.10 mol) of 1,4-dibromobutane and 15.0 g (0.101 mol) of phthalic anhydride is carried out to give the title compound.

Boiling point: 130–154° C./7 mmHg.

The solidified compound is crystallised from ethanol.

Melting point: 74–75° C.; Elemental microanalysis:

|              | C     | H    |
|--------------|-------|------|
| % calculated: | 76.57 | 6.43 |
| % found:      | 76.59 | 6.07 |

Preparation 7: 3,3-Spiro-pentamethylenephthalide

Analogous to the method described in Preparation 6, using 1,5-dibromopentane.

EXAMPLE 1

3-Butyl-6-nitro-phthalide

To 500 ml of filming nitric acid (sp. gr. 1.50) there are added, dropwise and with stirring, 190 g (1.0 mol) of the compound obtained in Preparation 1 at an internal temperature of 35–40° C., and the temperature is kept at 40–45° C. for 2 hours. The reaction mixture is put aside at room temperature overnight, and poured into crushed ice. The separated solid is collected and washed with water, dried and crystallised from ethanol to yield the title compound as white crystals.

Melting point: 53–55° C.; Elemental microanalysis:

|  | C | H |
|---|---|---|
| % calculated: | 61.27 | 5.57 |
| % found: | 61.11 | 5.44 |

EXAMPLE 2

3-Hexyl-6-nitro-phthalide

Analogously to the method described in Example 1, 11.7 g (0.054 mol) of compound obtained in Preparation 3 are nitrated to give the title compound as a yellow oil.

Elemental microanalysis:

|  | C | H |
|---|---|---|
| % calculated: | 63.86 | 6.51 |
| % found: | 63.57 | 6.72 |

EXAMPLE 3

6-Nitro-3-octyl-phthalide

Analogously to the method described in Example 1, 4.0 g (0.05162 mol) of compound obtained in Preparation 4 are nitrated to give the title compound as a yellow oil.

Elemental microanalysis:

|  | C | H |
|---|---|---|
| % calculated: | 65.96 | 7.27 |
| % found: | 66.11 | 7.55 |

EXAMPLE 4

6-Amino-3-butyl-phthalide

To a suspension of 141 g (0.6 mol) of compound obtained in Example 1 in 250 ml of ethanol there are added 14 g of 5% Pd—C catalyst. The mixture is hydrogenated at a pressure of 34 kg/cm². After the absorption of hydrogen has ceased, the hot mixture is filtered to remove the catalyst. The filter cake is washed with hot ethanol. On cooling, the crystals are separated and additional product is obtained from the condensed filtrate and washed to give the title compound.

Melting point: 129–131° C.; Elemental microanalysis:

|  | C | H |
|---|---|---|
| % calculated: | 70.23 | 7.37 |
| % found: | 70.13 | 7.05 |

EXAMPLE 5

6-Amino-3-hexyl-phthalide

Analogously to the method described in Example 4, 3.5 g (0.018 mol) of compound obtained in Example 2 are reduced to give the title compound.

Elemental microanalysis:

|  | C | H |
|---|---|---|
| % calculated: | 67.78 | 6.26 |
| % found: | 67.97 | 6.20 |

EXAMPLE 6

6-Amino-3-octyl-phthalide

Analogously to the method described in Example 4, 2.5 g (0.0086 mol) of compound obtained in Example 3 are reduced to give the title compound Melting point: 124–125° C.; Elemental microanalysis:

|  | C | H |
|---|---|---|
| % calculated: | 73.53 | 8.87 |
| % found: | 73.51 | 8.91 |

EXAMPLE 7

6-Acetamido-3-butyl-phthalide

A mixture of 0.3 g (1.55 mmol) of compound obtained in Example 4 and 3 ml of acetic anhydride and 1 drop of sulphuric acid is heated until dissolved and kept for 15 minutes. On cooling, white crystals are separated and recrystallised from ethanol to give the title compound.

Melting point: 138–139° C.; Elemental microanalysis:

|  | C | H |
|---|---|---|
| % calculated: | 67.99 | 6.93 |
| % found: | 67.67 | 6.75 |

EXAMPLE 8

6-Acetamido-3-hexyl-phthalide

Analogously to the method described in Example 7, 1.4 g (6.0 mmol) of compound obtained in Example 5 are acetylated to give the title compound.

Melting point: 135–137° C.; Elemental microanalysis:

|  | C | H | N |
|---|---|---|---|
| % calculated: | 69.79 | 7.69 | 5.09 |
| % found: | 69.61 | 7.71 | 4.82 |

EXAMPLE 9

6-Acetamido-3-octyl-phthalide

Analogously to the method described in Example 7, 0.5 g (1.91 mmol) of compound obtained in Example 6 is acetylated to give the title compound.

Melting point: 133–134° C.; Elemental microanalysis:

|  | C | H |
|---|---|---|
| % calculated: | 71.26 | 8.31 |
| % found: | 71.29 | 8.39 |

EXAMPLE 10

3-Butyl-6-formamido-phthalide

A solution of 3.07 g (0.015 mol) of the compound obtained in Example 4 in 15 ml of 85% formic acid is heated to 60° C. An hour later the reaction mixture is poured into ice-water. The separated solid is collected and crystallised from dilute ethanol to give the title compound.

Melting point: 127–129° C.; Elemental microanalysis:

|  | C | H | N |
|---|---|---|---|
| % calculated: | 66.93 | 6.48 | 6.01 |
| % found: | 66.75 | 6.62 | 5.79 |

EXAMPLE 11

3-Butyl-6-ethoxyformamido-phthalide

A mixture of 3.08 g (0.015 mol) of compound obtained in Example 4 and 10 ml of ethyl chloroformate is heated for 10 minutes. The excess ethyl chloroformate is removed in vacuo and the residue is washed with water and crystallised from dilute ethanol to give the title compound.

Melting point: 125–126° C.; Elemental microanalysis:

|  | C | H | N |
|---|---|---|---|
| % calculated: | 64.96 | 6.91 | 5.05 |
| % found: | 65.19 | 6.80 | 5.10 |

EXAMPLE 12

3-Butyl-6-pentanamido-phthalide

A mixture of 3.08 g (0.015 mol) of compound obtained in Example 4 and 5 ml of valeric anhydride is heated for 15 minutes. On cooling, the separated solid is collected and washed with water, and crystallised from dilute ethanol to give the title compound.

Melting point: 137–139° C.; Elemental microanalysis:

|  | C | H | N |
|---|---|---|---|
| % calculated: | 70.06 | 8.01 | 4.84 |
| % found: | 69.72 | 7.63 | 4.81 |

EXAMPLE 13

3-Butyl-6-carboxypropionamido-phthalide

A mixture of 3.08 g (0.015 mol) of compound obtained in Example 4 and 1.5 g of succinic anhydride is heated until melted and kept for 15 minutes. After 4 hours at room temperature the reaction mixture is dissolved in hot ethanol; the title compound is obtained as white crystals.

Melting point: 163–165° C.; Elemental microanalysis:

|  | C | H | N |
|---|---|---|---|
| % calculated: | 62.94 | 6.27 | 4.59 |
| % found: | 63.65 | 6.18 | 4.61 |

EXAMPLE 14

3-Butyl-6-(isopropylamino)-phthalide

To a solution of 4.1 g (20.0 mmol) of compound obtained in Example 4 in 4 ml of acetone and 96 ml of anhydrous ethanol there is added 10% Pd—C catalyst. The mixture is hydrogenated under a hydrogen pressure of 3–3.5 kg/cm$^2$. After the absorption of hydrogen is complete, the catalyst is filtered off and the filtrate is concentrated in vacuo to dryness. The residue is crystallised from dilute ethanol to give the title compound.

Melting point: 72–74° C.; Elemental microanalysis:

|  | C | H | N |
|---|---|---|---|
| % calculated: | 72.84 | 8.56 | 5.66 |
| % found: | 73.09 | 8.59 | 5.62 |

EXAMPLE 15

3-Butyl-6-(cyclopentylamino)-phthalide

Analogously to the method described in Example 14, 4.1 g (20.0 mmol) of compound obtained in Example 4 in 5 ml of cyclopentanone and 150 ml of 95% ethanol are added to 10% Pd—C catalyst and hydrogenated to give the title compound.

Melting point: 79–81° C.; Elemental microanalysis:

|  | C | H | N |
|---|---|---|---|
| % calculated: | 74.69 | 8.48 | 5.13 |
| % found: | 74.47 | 8.61 | 5.03 |

EXAMPLE 16

3-Butyl-6-(cyclohexylamino)-phthalide

Analogously to the method described in Example 14, 4.1 g (20.0 mmol) of compound obtained in Example 4 in 5 ml of cyclohexanone and 150 ml of 95% ethanol are added to 10% Pd—C catalyst and hydrogenated to give the title compound.

Melting point: 123–124° C.; Elemental microanalysis:

|  | C | H | N |
|---|---|---|---|
| % calculated: | 75.22 | 8.77 | 4.87 |
| % found: | 75.10 | 8.59 | 4.82 |

EXAMPLE 17

3-Butyl-6-bis(2-hydroxyethyl)amino-phthalide Hydrochloride

To a solution of 1.0 g (4.88 mmol) of the compound obtained in Example 4 in 20 ml of 70% acetic acid there are added, at 0° C., 15 ml of ethylene oxide, and the mixture is kept at 0° C. for 24 hours. The solvent is removed and the residue is dissolved in ethanol. Hydrogen chloride is passed through the solution. Anhydrous ether is added to make the solution turbid. The separated solid is collected to give the title compound.

Melting point: 149–151° C.; Elemental microanalysis:

|  | C | H |
|---|---|---|
| % calculated: | 58.27 | 7.33 |
| % found: | 58.57 | 7.43 |

EXAMPLE 18

3-Butyl-6-cyano-phthalide

A suspension of 7.2 g (32.12 mmol) of the compound obtained in Example 4 in 100 ml of 18% hydrochloric acid is diazotized by a solution of 6 g of sodium nitrite in 30 ml of water at 3–5° C. To this solution there is added, with vigorous stirring, a solution of cuprous cyanide, prepared from 21.0 g of $CuSO_4.5H_2O$ in 87 ml of $H_2O$ and 24.7 g of potassium cyanide in 133 ml of $H_2O$ at 50–60° C. The mixture is stirred at the same temperature for 2 hours. The separated solid is extracted with methylene chloride, the organic phase is washed with sodium carbonate solution and water. After removing the solvent, the residue is crystallised from ethanol to give the title compound.

Melting point: 85–86° C.; Elemental microanalysis:

|  | C | H | N |
|---|---|---|---|
| % calculated: | 72.56 | 6.00 | 6.51 |
| % found: | 72.58 | 5.88 | 6.38 |

EXAMPLE 19

3-Butyl-6-aminoformyl-phthalide

To a solution of 0.8 g (3.72 mmol) of compound obtained in Example 18 in 100 ml of acetone there is added a solution of 0.55 g of potassium carbonate in 5 ml of water, to which there are added, at 20° C., 14 ml of 30% hydrogen peroxide. The mixture is put aside at room temperature overnight. The solvents are removed in vacuo and the residue is washed with water and crystallised from ethanol, giving the title compound.

Melting point: 163–164° C.; Elemental microanalysis:

|  | C | H | N |
|---|---|---|---|
| % calculated: | 62.14 | 6.82 | 5.57 |
| % found: | 62.39 | 6.51 | 5.62 |

EXAMPLE 20

3-Butyl-6-ureido-phthalide

To a solution of 8.27 g (0.04 mol) of the compound obtained in Example 4 in 39.4 ml of glacial acetic acid there are added, with sting, 25 ml of water, and to this solution there is slowly added a solution of 6.54 g of potassium cyanate in 10 ml of water. Once a white precipitate appears, the remaining potassium cyanate solution is added in one portion immediately. The mixture is warmed at 55° C., and stirred for 1 hour, then put aside at room temperature for 3 hours. 50 ml of water are added and the mixture is cooled to 5° C.; the separated solid is collected and dissolved in 10% sodium carbonate solution. Any insoluble material is filtered off and the filtrate is acidified with dilute sulphuric acid. The solid is collected and washed with water and dried, giving the title compound.

Melting point: 196–199° C.; Elemental microanalysis:

|  | C | H |
|---|---|---|
| % calculated: | 62.89 | 6.62 |
| % found: | 62.64 | 6.41 |

EXAMPLE 21

3-Butyl-6-thioureido-phthalide

Analogously to the method described in Example 20, using potassium thiocyanate instead of potassium cyanate, the product is crystallised from ethanol, giving the title compound.

Melting point: 183–185° C.; Elemental microanalysis:

|  | C | H |
|---|---|---|
| % calculated: | 59.10 | 6.10 |
| % found: | 58.96 | 6.15 |

EXAMPLE 22

6-Amino-3-butyl-5-nitro-phthalide
Step A: 6-Acetamido-3-butyl-5-nitro-phthalide

To 100 ml of stirred and ice-cold turning nitric acid (sp. gr. 1.50) there are added, in portions, 59 g (0.288 mol) of compound obtained in Example 7 with the temperature below 10° C. The resulting clear solution is put aside at room temperature overnight. The reaction material is poured into crushed ice, and the solid is filtered, washed with water, dried and crystallised from ethanol, giving the title compound.

Melting point: 167–169° C.; Elemental microanalysis:

|  | C | H | N |
|---|---|---|---|
| % calculated: | 57.53 | 5.52 | 9.59 |
| % found: | 57.75 | 5.53 | 9.64 |

Step B: 6-Amino-3-butyl-5-nitro-phthalide

To a suspension of 29.2 g of compound obtained in Step A in 25 ml of 95% ethanol there are added 15 ml of hydrochloric acid and 20 ml of water. The mixture is refluxed for 3 hours and put aside at room temperature overnight The solvents are removed under reduced pressure. The residue is treated with 5% NaOH; the solid is collected and washed with water, dried, and crystallised from ethanol giving the title compound.

Melting point: 126–128° C.; Elemental microanalysis:

|  | C | H | N |
|---|---|---|---|
| % calculated: | 57.57 | 5.64 | 11.20 |
| % found: | 57.65 | 5.60 | 10.98 |

EXAMPLE 23

5,6-Diamino-3-butyl-phthalide

To a suspension of 3.75 g (15 mmol) of compound obtained in Example 22 in 150 ml of 95% ethanol there is added Raney nickel catalyst to hydrogenate at a hydrogen pressure of 1 kg/cm$^2$. After the absorption of hydrogen has ceased, the catalyst is filtered off, and the filtrate is concentrated to dryness. The residue is crystallised from dilute ethanol, giving the title product.

Melting point: 94–96° C.; Elemental microanalysis:

|  | C | H | N |
|---|---|---|---|
| % calculated: | 65.43 | 7.32 | 12.72 |
| % found: | 65.34 | 7.02 | 12.49 |

EXAMPLE 24

3,3-Diethyl-6-nitro-phthalide

Analogously to the method described in Example 1, from the compound of Preparation 5 the title compound is obtained.

Melting point: 98.5–100° C.

EXAMPLE 25

6-Amino-3,3-diethyl-phthalide

Analogously to the method described in Example 4, from the compound of Example 24 the title compound is obtained.

Melting point: 153–154° C.

EXAMPLE 26

6-Nitro-3,3-spiro-tetramethylene-phthalide

Analogously to the method described in Example 1, from the compound of Preparation 6 the title compound is obtained.

Melting point: 8183° C.

EXAMPLE 27

6-Amino-3,3-spiro-tetramethylene-phthalide

Analogously to the method described in Example 4, from the compound of Example 26 the title compound is obtained.

Melting point: 139–140° C.

EXAMPLE 28

6-(Dimethylamino)-3,3-spiro-tetramethylene-phthalide

Analogously to the method described in Example 14, the hydrogenation starting from the compound of Example 26, paraformaldehyde and 10% Pd—C catalyst in ethanol gives the title compound.

Melting point: 99–101° C.

EXAMPLE 29

6-Nitro-3,3-spiro-pentamethylene-phthalide

Analogously to the method described in Example 1, from the compound obtained in Preparation 7 the title compound is obtained.

Melting point: 110–112° C.

EXAMPLE 30

6-Amino-3,3-spiro-pentamethylene-phthalide

Analogously to the method described in Example 4, from the compound of Example 29 the title compound is obtained.

Melting point: 194.5–196° C.

EXAMPLE 31

6-(Dimethylamino)-3,3-spiro-pentamethylene-phthalide

Analogously to the method described in Example 14, the hydrogenation starting from the compound of Example 29, paraformaldehyde and 10% Pd—C catalyst in ethanol gives the title compound.

Melting point: 88–89° C.

EXAMPLE 32

3-Butyl-6-(3,5-di-tert-butyl-4-hydroxybenzamido)-phthalide 2.50 g (10 mmol) of 3,5-di-tert-butyl-4-hydroxy-benzoic acid are heated with 2.5 ml of thionyl chloride under reflux for 30 minutes. The reaction mixture is evaporated in vacuo and the residue is mixed with petroleum ether to remove the excess of thionyl chloride. 2.05 g (10 mmol) of compound obtained in Example 4 are mixed with 8.6 g of dry pyridine and dried ether. To this suspension there is added, dropwise, the ethereal solution of acyl chloride prepared above; the reaction mixture is refluxed for 30 minutes. The solvents are removed in vacuo. The residue is washed with water and dried. The title compound is crystallised from ethyl acetate.

Melting point: 189–190° C.

EXAMPLE 33

3-Butyl-6-(2-propyl-pentanamido)-phthalide 12.7 g of 2-propylvaleric acid are heated with 13 ml of thionyl chloride under reflux for 30 minutes. The reaction mixture is evaporated in vacuo and the residue is mixed with petroleum ether, which is removed to remove the excess of thionyl chloride. 16.4 g of the compound obtained in Example 4 are mixed with 35 g of dry pyridine. To this solution there is added, dropwise, the ethereal solution of acyl chloride prepared above; the reaction mixture is refluxed for 30 minutes and stirred at room temperature overnight The solvents are removed in vacuo. The residue is washed with water and dried. The title compound is crystallised from ethyl acetate.

Melting point: 125–126° C.; Elemental microanalysis:

|  | C | H | N |
|---|---|---|---|
| % calculated: | 72.46 | 8.82 | 4.24 |
| % found: | 72.25 | 8.90 | 4.33 |

EXAMPLE 34a (+)-(3R)-6-Amino-3-butyl-phthalide

Step A: (+)-(3R)-6-Amino-3-butyl-phthalide (+)-Tartrate

A hot solution of 10.26 g (0.05 mol) of compound obtained in Example 4 in 115 ml of anhydrous methanol is mixed with a warm solution of 7.51 g (0.05 mol) of (+)-tartaric acid in 60 ml of methanol. The mixture is put aside at room temperature overnight, and then at 0–5° C. for 2 hours. The separated crystals are collected and washed with a small amount of methanol to give white crystals. Recrystallisation from methanol (1:8) three times gives the title compound containing one molecule of methanol, as white needles.

Melting point: 152–154° C.; $[\alpha]_D$=+51.36 (20° C., methanol 3.07%).

Step B: (+)-(3R)-6-Amino-3-butyl-phthalide

To a hot solution of 2.26 g of compound obtained in Step A in methanol there are added 36 ml of distilled water. The resulting mixture is heated to a clear solution and gradually cooled. The separated long white crystals are collected and washed with water, obtaining the title compound containing one molecule of methanol.

Melting point: 128–129° C.; $[\alpha]_D$=+89.69 (17° C., methanol 1.465%).

EXAMPLE 34b (−)-(3S)-6-Amino-3-butyl-phthalide

Process analogous to Example 34a starting from Example 4 and replacing (+)-tartaric acid by (−)-tartaric acid.

Melting point: 127–129° C.; $[\alpha]_D$=−87.1 (17° C., methanol 1%).

EXAMPLE 35

6-Isopropylamino-3,3-spiro-tetramethylene-phthalide

Process analogous to Example 14 starting from Example 26.

EXAMPLE 36

3-Butyl-6-(dimethylamino)-phthalide

Process analogous to Example 31 starting from Example 1.

EXAMPLE 37

3-Butyl-6-[(2-bromopentanoyl)amino]-phthalide

Process analogous to Example 7 replacing acetic anhydride by 1-bromopentanoic anhydride.

EXAMPLE 38

3-Butyl-6-methoxyformamido-phthalide

Process analogous to Example 11 replacing ethyl chloroformate by methyl chloroformate.

PHARMACOLOGICAL STUDY OF THE COMPOUNDS OF THE INVENTION

EXAMPLE A

Acute Toxicity Study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals ) was evaluated and demonstrated the low toxicity of the compounds of the invention.

EXAMPLE B

Ion Channel Blockers

Compounds of the invention antagonise intracellular $Ca^{+2}$ level induced by KCl, Bay K 8644 and glutamate. Using patch clamp whole cell recording technique, compounds of the invention are found to be able to reduce the L-type calcium current and to shorten the action potential duration in myocardial cells of guinea pigs and cultured human neuroblastoma cells.

Using a patch clamp whole cell recording technique in myocardial cells of guinea pigs, the compounds of the invention have been shown to reduce in a concentration-dependent and reversible manner the L-type calcium current and to block the sodium current. These results indicate that the compounds of the invention could be potent L-type calcium channel and sodium channel blockers.

EXAMPLE C

Glutamate-neurotoxicity Antagonistic Effect

Glutamate is a major excitatory neurotransmitter in the central nervous system and there is excessive release of glutamate in the case of cerebral ischemia Compounds of the invention at concentration of $10^{-6}$ mol/L can remarkably inhibit calcium-dependent and also calcium-independent release of glutamate in synaptosomes.

EXAMPLE D

Transient Global Forebrain Ischaemia in the Wistar Rat

Transient forebrain ischaemia was induced by four-vessel occlusion according to the method of Pulsinelli and Brierley (Stroke, 1979, 10: 267–272). Male Wistar rats (280–320 g) were prepared for forebrain ischaemia under pentobarbital (60 mg/kg i.p.) anaesthesia The vertebral arteries were definitively occluded by electrocauterisation and atraumatic clamps were placed around the carotid arteries without interrupting the arterial blood flow. The following day, animals were administered, by the i.p. route, the compound under study (20 mg/kg) in Tween/saline (2 ml/kg) or with the carrier alone, and 30 min later cerebral ischaemia was induced in the unanaesthetised animal by tightening the clamps for 10 mm. Carotid clamping results, within 1–2 min, in a loss of the righting reflex. Consequently, failure of animals to lose consciousness indicated that the ischaemia was not complete, and precluded the animal from the study. Body temperature was monitored with a rectal temperature probe and maintained (36.5–37.5° C.) with heated lamps until awakening from the anaesthesia. Thereafter animals were housed individually with free access to food and water. Seven days later animals were sacrificed by decapitation, the brains were rapidly removed, and frozen at −30° C. in isopentane and stored at −40° C. until analysis. Neuronal cell death was assessed by counting viable cells in the CA1 field of the hippocampus in both hemispheres (from 3.8 to 4.2 mm anterior to L.A. line) in 7 μm hematoxylin-eosin-stained brain sections.

Results indicate that the compounds of the invention at a dose of 20 mg/kg i.p. possess potent neuroprotective effects that block the neuronal death induced by transient global forebrain ischaemia in the rat.

EXAMPLE E

Effects of Compounds of the Invention on MCAO in Rats (Tamura A. and col, J. Cereb. Blood flow Metab., 1981, 1, 53–56)

Compounds of the invention are also shown to possess the anticerebral ischemic effect. Administered ip 20 mg/kg 0.5 hours before or 2 hours after MCAO, they decrease the stroke index, brain edema and infact volume in MCAO rats.

EXAMPLE F

Maximum Electric Shock Seizures in NMRI Mice

Adult male NMRI mice (18–20 g) were used. Mice were maintained on an adequate diet and allowed free access to food and water before testing. The drug under study or the carrier was administered by the i.p. or p.o. route 30 min or 60 min before testing, respectively. Then, mice were placed in individual cage units (10×10×10 cm) to avoid group effects. A drop of electrolyte solution (0.9% sodium chloride solution) was applied to the eyes and an electrical stimulus (20 mA; 50 Hz) was delivered for 0.5 sec. The animals were restrained only by hand and were released at the moment of stimulation in order to permit observation of the seizure throughout its entire course. The hindleg tonic extensor component was rated present or absent (1 or 0) and was considered to have been suppressed by a drug effect if it did not exceed a 90° angle with the plane of the body. The results indicate that exemplified compounds have potent anticonvulsant effects from 25 to 50 mg/kg i.p. and at a dose of 100 mg/kg p.o.

EXAMPLE G

Social Recognition Test in the Wistar Rat

Adult Wistar rats were submitted to a social recognition test which investigates a form of episodic memory in the rat. Each rat was exposed to a juvenile rat in two encounters (5 min each), the two encounters being separated by an interval of two hours. The time (sec) spent in investigating the juvenile was recorded, a decrease in investigation time on the second encounter indicating that the rat recognised the juvenile. In control rats, the investigation times were the same for the two encounters demonstrating that the animals no longer recognised the juvenile rat in the second encounter. Statistical analyses were performed on the difference in investigation time between the two encounters. Treatment (10 mg/kg i.p.) with compounds of the invention immediately after the first encounter reduced significantly the investigation of the juvenile on the second encounter. The results suggest that our compounds possess cognition-enhancing properties by modulating post-training neurobiological processes underlying memory storage.

EXAMPLE H

Pharmaceutical Composition

Formulation for the preparation of 1000 tablets each comprising 10 mg of active ingredient:

| | |
|---|---|
| 6-Amino-3,3-spiro-tetramethylene-phthalide (Example 27) | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

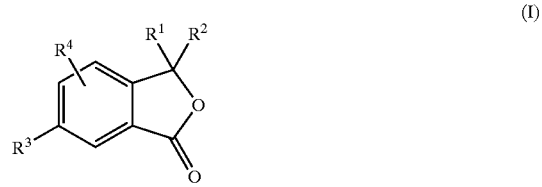

wherein:
R$^1$ represents linear or branched (C$_1$–C$_{12}$)alkyl or ureido,
R$^2$ represents hydrogen or linear or branched (C$_1$–C$_{12}$) alkyl,
or R$^1$ and R$^2$, together with the carbon atom carrying them, form a 5 or 6 carbon cycloalkyl group, R³ represents a group selected from CN, NO₂, NR$_a$R'$_a$, NR$_a$SO₂R'$_a$, NR$_a$CZR⁵ and CZNR$_a$R'$_a$ wherein:

Z represents oxygen or sulphur,

R⁵ represents a group selected from OR$_a$, R$_a$ and NR$_a$R'$_a$ wherein R$_a$ and R'$_a$, which may be the same or different, represent hydrogen or linear or branched (C₁–C₆)alkyl, (C₃–C₈)cycloalkyl, (C₃–C₈)cycloalkyl-(C₁–C₆)alkyl in which the alkyl moiety is linear or branched, phenyl or phenyl-(C₁–C₆)alkyl in which the alkyl moiety is linear or branched, R⁴ represents hydrogen or R³ as defined hereinbefore, it being understood that:

the phenyl or phenylalkyl may be substituted on the benzene ring by one or more substituents selected from linear or branched (C₁–C₆)alkyl, hydroxy, linear or branched (C₁–C₆)alkoxy, amino, linear or branched (C₁–C₆)alkylamino, di-(C₁–C₆)alkylamino in which each alkyl moiety is linear or branched, NO₂ and halogen, the alkyl group may be substituted by one or more substituents selected from hydroxy, carboxy, linear or branched (C₁–C₆)alkyl, linear or branched (C₁–C₆) alkoxy and halogen, the cycloalkyl and cycloalkylalkyl groups may be substituted on the cyclic moiety by one or more substituents selected from hydroxy, carboxy, linear or branched (C₁–C₆)-alkoxy and halogen, and provided that the compound of formula (I) is other than the following compounds: 3-methyl-, 3-ethyl-, 3,3-dimethyl- or 3,3-diethyl-6-nitro-phthalide; or 3-methyl- or 3,3-dimethyl-6-amino-phthalide; or 3,3-dimethyl-6-(dimethylamino)-phthalide;

its enantiomers, diastereoisomers, and pharmaceutically acceptable acid or base additional salts thereof.

2. A compound of claim 1, wherein R⁴ represents hydrogen.

3. A compound of claim 1, wherein R¹ represents linear or branched (C₁–C₁₂)alkyl.

4. A compound of claim 1, wherein R¹ and R², together with the carbon atom carrying them, form a 5 or 6 carbon ring.

5. A compound of claim 1, wherein R³ represents NO₂.

6. A compound of claim 1, wherein R³ represents NR$_a$R'$_a$.

7. A compound of claim 1, wherein R³ represents NH₂.

8. A compound of claim 1 which is selected from 6-amino-3-butyl-phthalide, its enantiomers, and addition salts thereof with a pharmaceutically acceptable acid or base.

9. A compound of claim 1 which is selected from (+)-(3R)-6-amino-3-butyl-phthalide and its addition salts thereof with a pharmaceutically acceptable acid or base.

10. A compound of claim 1 which is selected from 3-butyl-6-isopropylamino-phthalide, its enantiomers, and addition salts thereof with a pharmaceutically acceptable acid or base.

11. A compound of claim 1 which is selected from 6-amino-3,3-spiro-tetramethylene-phthalide and its addition salts thereof with a pharmaceutically acceptable acid or base.

12. A compound of claim 1 which is selected from 3-butyl-6-formamido-phthalide and its addition salts thereof with a pharmaceutically acceptable acid or base.

13. A compound of claim 1 which is selected from 6-amino-3,3-diethyl-phthalide and its addition salts thereof with a pharmaceutically acceptable acid or base.

14. A method of treating a living animal body afflicted with epilepsy, cognitive deficiencies in memory associated with ageing, and neurodegenerative diseases, comprising the step of administering to the living animal body an amount of a compound of claims 1 which is effective for the alleviation of the condition.

15. A pharmaceutical composition comprising, as active principle, an effective amount of a compound of claim 1 together with one or more pharmaceutically acceptable excipients or vehicles.

16. A method of claim 14 wherein the neurodegenerative diseases are selected from Alzheimer's disease, Parkinson's disease, Pick's disease, Korsakoff's disease and frontal lobe and subcortical dementias, cronic neurodegenerative diseases, and cerebral ischemia.

* * * * *